(12) United States Patent
Vancamberg et al.

(10) Patent No.: US 11,937,970 B2
(45) Date of Patent: Mar. 26, 2024

(54) SYSTEM AND METHOD FOR CALIBRATING A CAMERA FEATURE DETECTION SYSTEM OF AN X-RAY SYSTEM

(71) Applicant: GE Precision Healthcare LLC, Wauwatosa, WI (US)

(72) Inventors: Laurence Vancamberg, Poissy (FR); Gregory Stratton, Wauwatosa, WI (US); Rakesh S. Bhat, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 56 days.

(21) Appl. No.: 17/737,352

(22) Filed: May 5, 2022

(65) Prior Publication Data
US 2023/0355201 A1    Nov. 9, 2023

(51) Int. Cl.
*A61B 6/00* (2006.01)
*A61B 6/58* (2024.01)
*G01T 7/00* (2006.01)
*G06T 7/35* (2017.01)
*G06T 7/80* (2017.01)

(52) U.S. Cl.
CPC ............ *A61B 6/585* (2013.01); *A61B 6/4435* (2013.01); *A61B 6/4452* (2013.01); *A61B 6/584* (2013.01); *G01T 7/005* (2013.01); *G06T 7/35* (2017.01); *G06T 7/80* (2017.01); *A61B 2560/0228* (2013.01); *G06T 2207/10024* (2013.01); *G06T 2207/10048* (2013.01); *G06T 2207/10116* (2013.01)

(58) Field of Classification Search
None
See application file for complete search history.

(56) References Cited

U.S. PATENT DOCUMENTS

| | | |
|---|---|---|
| 9,438,897 B2 | 9/2016 | Barreto et al. |
| 10,835,199 B2 | 11/2020 | Chtcheprov et al. |
| 2019/0000407 A1* | 1/2019 | Muller ............... A61B 6/505 |
| 2019/0021677 A1* | 1/2019 | Grbic ................. G06T 7/11 |
| 2020/0268339 A1* | 8/2020 | Hao .................. G06T 7/0014 |
| 2021/0201476 A1* | 7/2021 | Prasad .............. G06T 7/0012 |
| 2022/0225957 A1* | 7/2022 | Kelly ................ A61B 6/582 |

* cited by examiner

*Primary Examiner* — Hoon K Song
(74) *Attorney, Agent, or Firm* — Boyle Fredrickson, S.C.

(57) ABSTRACT

Various methods and systems are provided for calibrating a camera-based feature detection system for an x-ray system having a support surface, and a gantry operably connected to the support surface and a light source disposed on the gantry, where the gantry defines a system referential. The x-ray system includes a camera spaced from the gantry and operably connected to a calibration system, the camera defining a camera referential within which the support surface and gantry are positioned. The calibration system registers the camera referential to the system referential by operating the light source to position an indication on the support surface and by obtaining a number of camera images of the indication on the support surface and corresponding indication location in the system referential.

20 Claims, 8 Drawing Sheets

SYSTEM AND METHOD FOR CALIBRATING A CAMERA FEATURE DETECTION SYSTEM OF AN X-RAY SYSTEM

FIELD OF THE DISCLOSURE

The present disclosure is related to the field of medical diagnostic imaging. More specifically the present disclosure is directed to systems and methods of medical imaging particularly related to body composition analysis and/or bone densitometry.

BACKGROUND OF THE DISCLOSURE

In medical x-ray imaging, for example, body composition and/or bone densitometry systems, an x-ray source and an x-ray detector are generally mounted on opposing ends of a substantially C-shaped gantry. A scanning radiographic technique, such as typically employed with densitometry, uses a narrowly collimated beam of radiation formed into, for example a fan beam. The emitted fan beam of radiation, typically x-rays, are incident on and detectable by the x-ray detector, although other configurations of x-ray imaging systems are known. This typically uses a smaller array for the x-ray detector, and the x-ray source and the x-ray detector are moved relative to the patient. In embodiments, this enables scanning or collection of data from a broad area of the patient, including the entire patient, as compared to other conventional radiography techniques. The source and the detector are positioned such that when an object (e.g., part of a human body) is interposed there between and is irradiated with x-rays, the detector produces data representative of characteristics of the interposed object.

In the particular application of densitometry, when two (or more) energies of x-rays are used, bone and tissue information can be acquired due to the differences in the absorption of the x-rays of different energies. Measurements of the x-ray absorption by an object at two different x-ray energies can reveal information about the composition of that object as decomposed into two selected basis materials. In the medical area, the selected basis materials are frequently bone and soft tissue. The ability to distinguish bone from surrounding soft tissue allows x-ray images to yield quantitative information about in vivo bone density for the diagnosis of osteoporosis and other bone disease.

Figure 1:
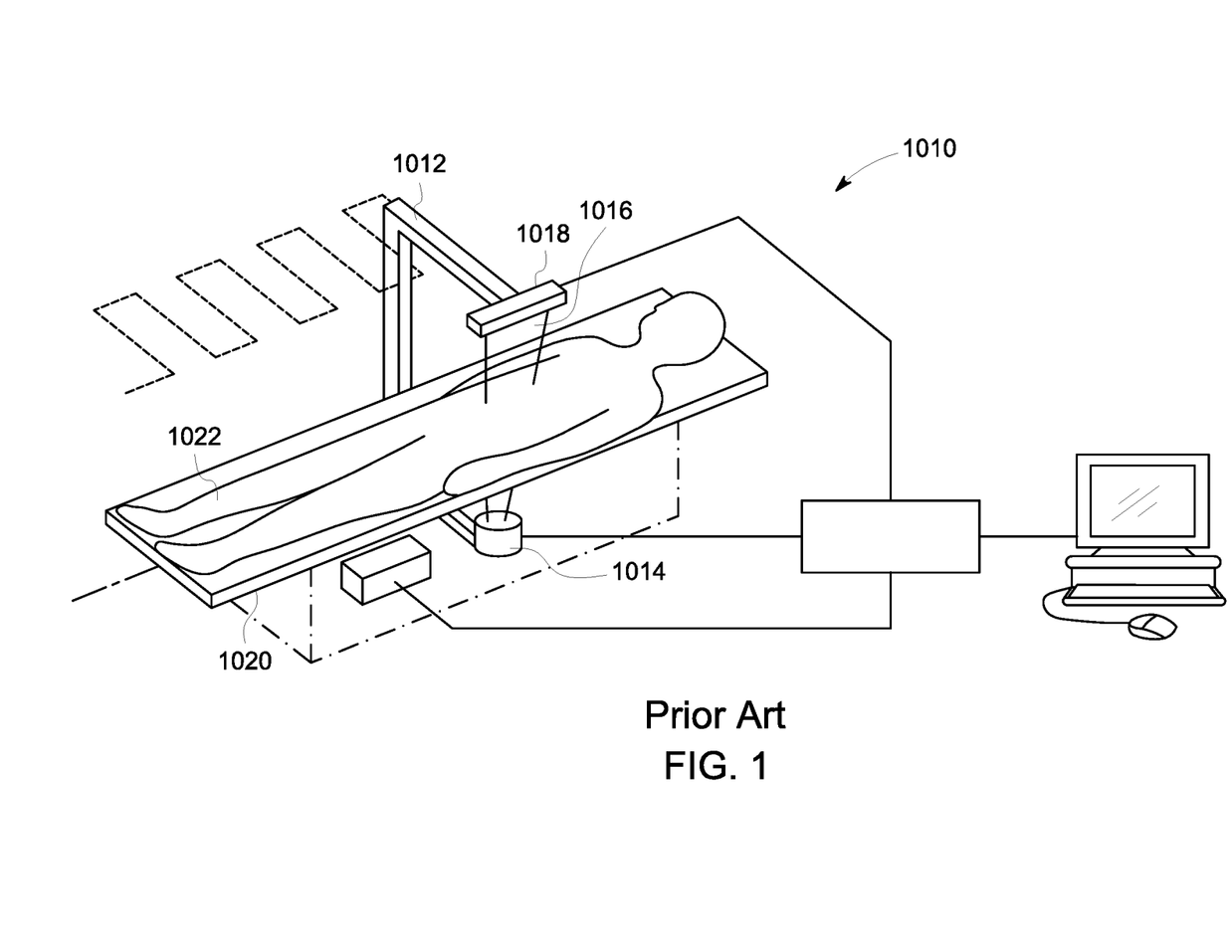
FIG. 1 is a schematic illustration of a prior art DXA system including an external camera.

As depicted in FIG. 1 an exemplary x-ray system, such as a dual energy x-ray absorptiometry (DXA or DEXA)/densitometry system 1010 may be configured to include a substantially C-shaped or semi-circular gantry, or C-arm 1012. The C-arm 1012 movably supports a source 1014 and a detector 1018 mounted opposite to each other on opposed ends. The patient 1022 is disposed between the source 1014 and the detector 1018, such as on a table 1020. In many systems 1010, the positions of the source 1014 and detector 1018 are variable in order to accommodate different patient morphologies, different orientations of the source 1014 and the detector 1018 for imaging different portions of the patient, etc. The movement of the source 1014 and the detector 1018 is normally controlled by a motor (not shown) located within the system 1010 to control and maintain the alignment of the source 1014 and the detector 1018 during the operation and/or alteration of the orientation of the system 1010.

In order to assist with and/or improve one or more of the proper positioning of the patient on the table 1020, automatic positioning of the source 1014 and detector 1018 relative to the patient, and/or the determination of the current field of view (FOV) of the source 1014 relative to the position of the patient 1022, the system 10 can employ a camera 1024 disposed outside of the system 1010, such as on a ceiling in a room in which the system 1010 is disposed. The camera 1024 provides optical images of the system 1010 and the patient in order to provide information to the system 1010 and/or operator of the system 1010 to streamline the operation of the system 1010 and reduce errors.

In order to enable the camera 1024 to provide the relevant information on the relative position of the source 1014/detector 1018 and the patient, the camera 1024 must be calibrated with regard to the system 1010, such that the position of objects in the images obtained by the camera 1024 can be referenced with regard to the same objects in the images obtained by the system 1010.

Figure 2:
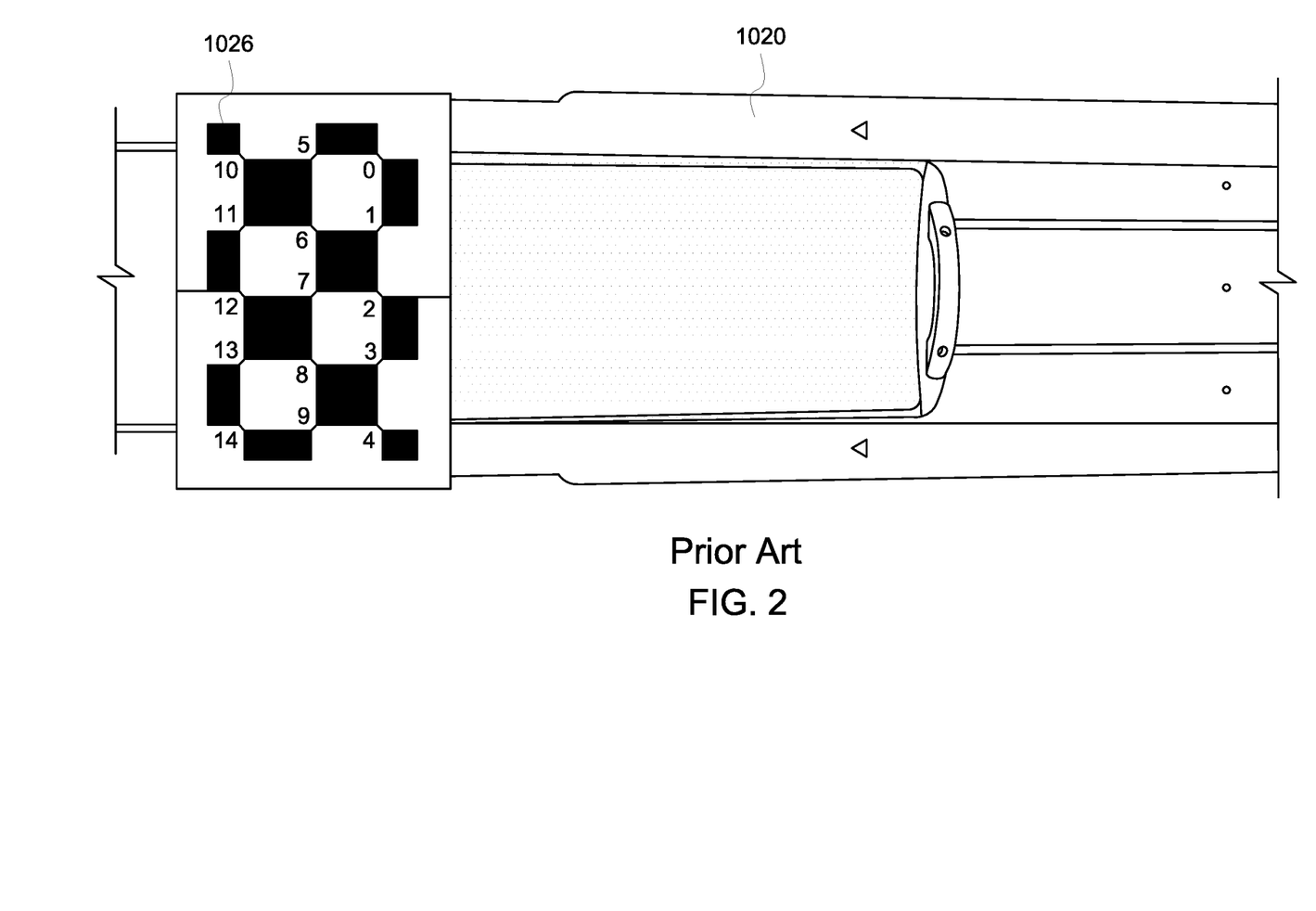
FIG. 2 is a schematic view of an optical marker used with the DXA system of FIG. 1

In order to perform the calibration, the system 1010 can employ a calibration optical marker 1026, such as that disclosed in U.S. Pat. No. 10,835,199 entitled Optical Geometry Calibration Devices, Systems, And Related Methods For Three-Dimensional X-Ray Imaging (the '199 patent), the entirety of which is expressly incorporated herein by reference for all purposes. The calibration optical marker 1026 is positioned on a portion of the system 1010, i.e., on the table 1020, and has a configuration, such as a chessboard pattern with known characteristics, e.g., square locations and sizes, that is able to be imaged by the camera 1024 and which location is known in regards to the image area 1018 or the table 1020.

In the calibration procedure, an image of the optical marker 1026 is obtained via the camera 1024. Using the known distances between the detector 1018 or the table 1020 and the marker 1026 and subsequently all squares intersection points on 1026 as a result of the known position, i.e., height, of the detector 1018 relative to the table 1020 and the position of the detector 1018 along the table 1020 caused by the movement of the motor (not shown) as controlled by the system 1010, and the calculated distances of the camera 1024 to the optical marker 1026 determined from the camera images such as those disclosed in the '199 patent, it is possible to register the camera images to the detector images to correlate coordinates in the camera images directly with coordinates in the detector images. With this registration, in any subsequent imaging procedure using the system 1010, images obtained by the camera 1024 can be used to determine the location of the patient relative to the source 1014/detector 1018 and the FOV of the source 1014 in order to provide the operator with any necessary adjustments to the position of the patient on the table 1020 to allow the system 1010 to provide the desired x-ray images of the patient.

However, while the use of the optical marker 1026 enables the calibration of the camera 1024 with regard to the system 1010 as described previously, the requirement for the optical marker 1026 is undesirable as it creates the need for an additional component that must be manufactured and sent to the deployment location for the system 10 for use in the calibration procedure.

As a result, it desirable to develop a system and method for the calibration of a camera with regard to a DXA/DEXA imaging system that avoids the need for a separate optical marker.

SUMMARY OF THE DISCLOSURE

According to one aspect of an exemplary embodiment of the disclosure, an x-ray system includes a support surface, and a gantry operably connected to the support surface and including an x-ray source, an x-ray detector alignable with the x-ray source, and a laser disposed on the gantry adjacent the x-ray detector, the gantry defining a system referential, an image processing system operably connected to the gantry to control the operation of laser, and the x-ray source and x-ray detector to generate x-ray image data, the image processing system including a processing unit for processing the x-ray image data from the detector, a database operably connected to the processing unit and storing instructions for operation of a calibration system, a display operably connected to the image processing system for presenting information to a user, and a user interface operably connected to the image processing system to enable user input to the image processing system and a camera-based feature detection system including a camera spaced from the gantry and operably connected to the image processing system, the camera defining a camera referential within which the support surface and gantry are positioned and operable to generate one or more camera images of the support surface and gantry, wherein the calibration system is operable to register the camera referential to the system referential, wherein the calibration system is configured to determine a number of positions of the indication within the camera image referential, to determine a number of positions of the indication within the system referential, and to register the camera referential to the system referential.

According to still another aspect of an exemplary embodiment of the present disclosure, a method for calibrating a camera-based feature detection system for an x-ray system including the steps of providing an x-ray system having a support surface, and a gantry operably connected to the support surface and including an x-ray source, an x-ray detector alignable with the x-ray source, and a laser disposed on the gantry adjacent the x-ray detector, the gantry defining a system referential, an image processing system operably connected to the gantry to control the operation of laser, and the x-ray source and x-ray detector to generate x-ray image data, the image processing system including a processing unit for processing the x-ray image data from the detector, a database operably connected to the processing unit and storing instructions for operation of a calibration system, a display operably connected to the image processing system for presenting information to a user, and a user interface operably connected to the image processing system to enable user input to the image processing system and a camera-based feature detection system including a camera spaced from the gantry and operably connected to the image processing system, the camera defining a camera referential within which the support surface and gantry are positioned and operable to generate one or more camera images of the support surface and gantry, wherein the calibration system is operable to register the camera referential to the system referential, operating the laser to position an indication on the support surface, obtaining a number of camera images of the indication on the support surface, determining a number of positions of the indication within the camera image referential, determining a number of positions of the indication within the system referential, and registering the camera referential to the system referential.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The description herein relates to various embodiments of medical imaging systems. In particular, methods and systems are provided for use as a single energy x-ray absorptiometry (SXA) system, as is exemplarily used to measure breast density or a dual-energy x-ray absorptiometry (DXA) used to measure bone mineral density. Examples of DXA are used herein although it will be recognized that in other embodiments, other modalities of radiography and/or medical imaging may be employed. For example, these may include, but are not limited to: PET, SPECT, C-arm angiography, mammography, ultrasound, and so forth. The present discussion of DXA is provided as an example of one suitable application.

Figure 3:
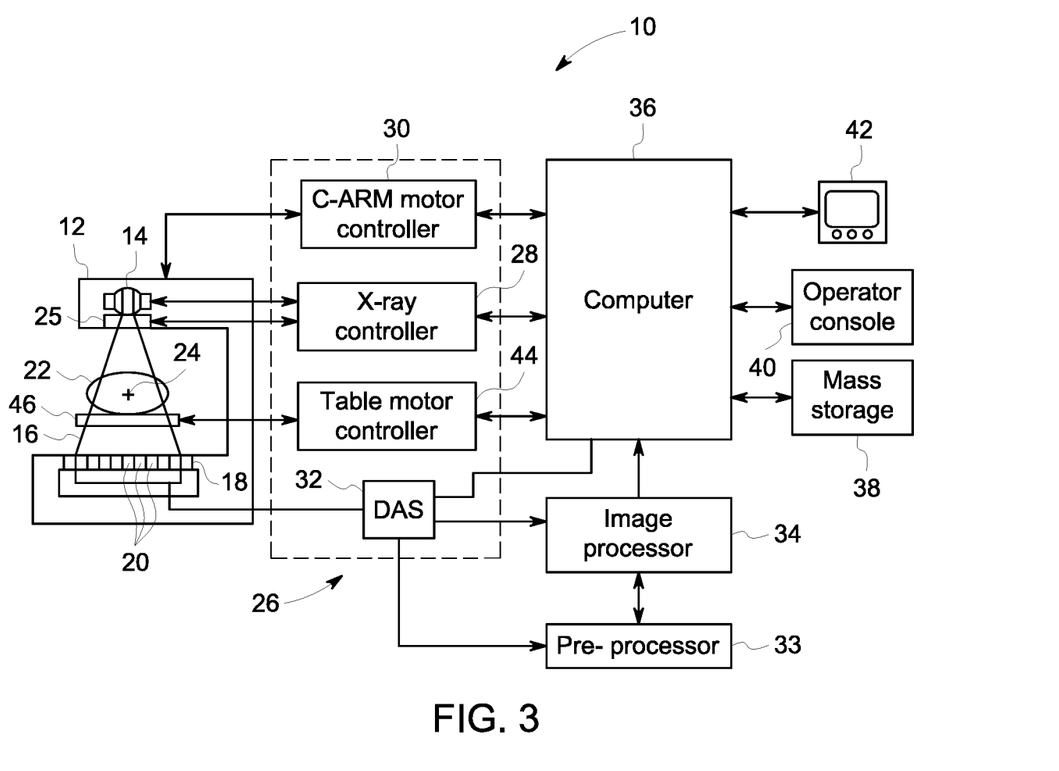
FIG. 3 is a block schematic diagram of an exemplary imaging system including the camera feature detection system and calibration system according to an exemplary embodiment of the disclosure.
Figure 4:
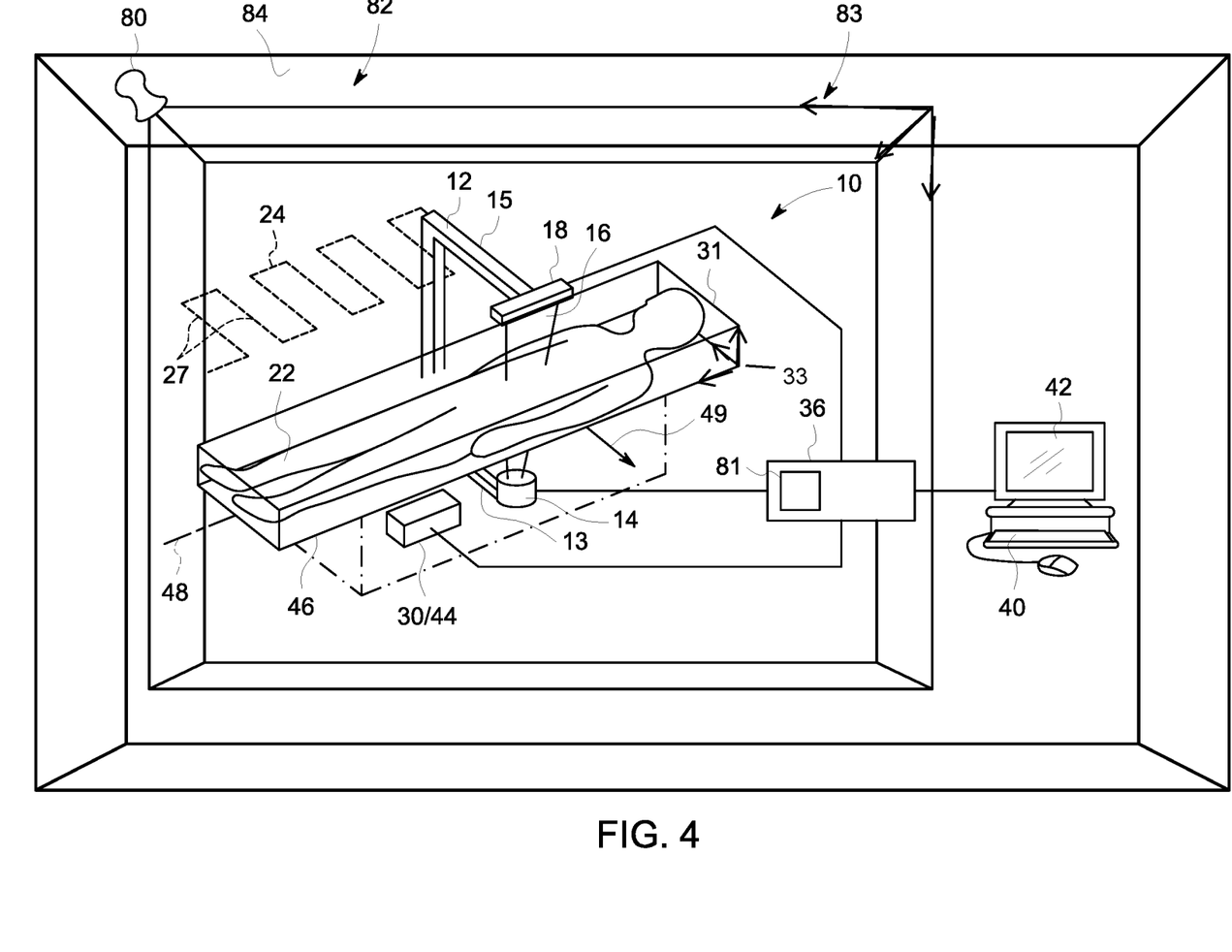
FIG. 4 is a schematic diagram of an exemplary DXA system including the camera feature detection system and calibration system according to an exemplary embodiment of the disclosure.

Referring to FIGS. 3 and 4, an exemplary embodiment of the system 10, such as that disclosed in US Patent Application Publication No. US2019/0000407, entitled Variable Distance Imaging, the entirety of which is hereby expressly incorporated by reference for all purposes, may be utilized to measure at least an area of a bone, a length of bone, a bone mineral content (BMC), a bone mineral density (BMD), or a tissue thickness or density. The BMD is calculated by dividing the BMC by the area of a bone. During operation, an x-ray beam with broadband energy levels is utilized to scan an object, for example, to scan a human patient to image the bones of the patient. The acquired images of the bones are used to diagnose a medical condition, for example osteoporosis. The images may be generated in part from determined bone density information acquired during a dual-energy x-ray scan. As described in further detail herein, the positions of the source 14, detector 18, and/or table can be adjusted to achieve further desired imaging purposes, including but not limited to magnification, increasing image resolution, or spatial resolution. For exemplary purposes, the imaging system 10 may be described as a dual-energy x-ray absorptiometry (DXA) system, although it will be recognized that a variety of other systems may also be implemented in a similar manner.

The imaging system 10 is shown as including a gantry 12. Gantry may be a substantially C shaped or semi-circular gantry, or C-arm gantry. The gantry 12 movably supports a source 14 and a detector 18 mounted opposite to each other on opposed ends. Further, a subject 22 is disposed between the source 14 and the detector 18.

Gantry 12 includes an x-ray source 14 that projects a beam of x-rays 16 toward detector array 18. The gantry 12 exemplarily includes a lower end 13 that is positioned below a subject 22, such as a patient, and an upper end 15 that is positioned above the subject 22. The x-rays pass through the subject 22 to generate attenuated x-rays. As depicted in FIG. 3, the x-ray source 14 may be secured to the upper end 15 and the x-ray detector 18 secured to the lower end 13. As depicted in FIG. 4, the detector 18 may be secured to the upper end 15 and the x-ray source 14 may be secured to the lower end 13. Each detector element 20 is exemplarily, but not limited to a cadmium telluride (CdTe) detector element, which produces an electrical signal that represents an intensity of the attenuated x-rays.

During a scan to acquire image data, gantry 12 and/or components mounted on gantry 12 are movable relative to the subject 22 and/or a table 46. The table 46 may include a scanning surface on which the subject 22 may be positioned. For example, during an acquisition of image data, the gantry 12 is movable to change a position and/or orientation of the source 14 and/or detector 18 relative to the patient. In an exemplary embodiment, the gantry 12 may move the source 14 and the detector 18 in a transverse scanning path, a progressive overlapping scanning path, or a zig-zag (e.g. raster) scanning path 24 that moves along both the long axis 48 and the short axis 49 of the table 20, as shown in FIGS. 3 and 4. It will be recognized that other forms of image data acquisition may utilize other forms of scanning paths, which may include, but are not limited to rotation or tilt of the gantry 12. It will be recognized that in other exemplary imaging systems within the present disclosure, one of the source or detector may remain in a fixed position while the other of the source or detector is movable with respect to the patient. In still other exemplary embodiments as disclosed herein, the table, which is configured to support the patient, is further movable to achieve a desired image acquisition.

Movement of the gantry 12 and an operation of x-ray source 14 are governed by an imaging controller 26 of imaging system 10. Imaging controller 26 includes an x-ray controller 28 that provides power and timing signals to x-ray source 14. The x-ray controller 28 may further provide operational and/or control signals to the adjustable collimator 25 to shape the beam of x-rays from the source 14 in accordance with the imaging procedure to be performed. In some embodiments, the x-ray beam may be shaped (collimated) as a fan beam. In an exemplary embodiment, the fan beam 16 may be a narrow fan beam such as to limit the divergence between x-rays in the beam, which has been shown to improve parallax and image overlap blurring.

The imaging controller 26 further includes a gantry motor controller 30 that controls a motion, speed, and position of gantry 12 via one or more suitable motors (not shown) operably connected to the gantry 12 or specified portions thereof and the gantry motor controller 30. In some embodiments, gantry motor controller 30 may control movement of the gantry 12 in multiple degrees of freedom utilizing the one or more motors, including a tilt angle of gantry 12. The system 10 can also include a table motor controller 44 is operably connected to the table 46 through a table motor (not shown) and to the imaging controller 26. The table motor is operable, under control signals from the table motor controller 44, to translate, rotate, and/or tilt the table 46 in a plurality of degrees of freedom of movement. In an embodiment, the table motor is operable to move the table 46 in three degrees of freedom, (e.g. horizontal, vertical, and depth translation) while in another embodiment, rotational degrees of freedom of movement (e.g. pitch, yaw, and roll) may be available. It will be recognized that the table motor may include one or more mechanical or electromechanical systems to carry out these movements of the table 46, including but not limited to tack and opinion, screw, or chain driven actuators.

The x-ray source 14 and the x-ray detector 18, i.e., the gantry 12, may be moved in a raster pattern 24 so as to trace a series of transverse scans 27 of the subject 22 during which dual energy x-ray data is collected by the x-ray detector 18. The transverse scanning procedure generates either a single image or quantitative data set, form a plurality of scan images acquired across a patient, wherein the x-ray source 14 and the detector 18 are either longitudinally aligned with the superior-inferior axis of the patient or transversely from the patient's left to right. Scanning a patient using a transverse motion facilitates minimizing the time between acquisitions of adjacent scan images because the transverse direction across the patient is shorter than the longitudinal direction across the patient. Thus transverse scanning can reduce the severity of patient motion artifacts between scan images allowing the images to be more accurately merged.

The transverse scanning motion is produced by coordination between the motion control of the gantry 12, x-ray source 14, and the x-ray detector 18 by the gantry motor controller 30 as well as optional control of the table 46 by the table motor controller 44 which operates the table 46 through the table motor. During operation, the x-ray source 14 produces a fan beam 16 having a plane that is exemplarily parallel to the longitudinal axis 48. Optionally, the fan beam 16 may have a plane that is perpendicular to the longitudinal axis 48. The raster pattern 24 is adjusted such that there is some overlap (e.g., an overlap of 10%) between successive scan lines of the fan beam 16. Further, the range of motion of the gantry 12 and the source 14/detector 18 define a system referential 31 encompassing the space able to the viewed/imaged by the system 10.

A data acquisition system (DAS) 32 in the imaging controller 26, samples and digitizes the data from detector elements 20 and converts the data to sampled and digitized data for subsequent processing. In some embodiments, DAS 32 may be positioned adjacent to detector array 18 on gantry 12. Pre-processor 33 receives the sampled and digitized data from DAS 32 to pre-process the sampled and digitized data. In one embodiment, pre-processing includes, but is not limited to, an offset correction, a primary speed correction, a reference channel correction, an air-calibration, and/or applying a negative logarithmic operation. As used herein, the term processor is not limited to just those integrated circuits referred to in the art as a processor, but broadly refers to a controller, a microcontroller, a microcomputer, a programmable logic controller, an application specific integrated circuit, and any other programmable circuit, and these terms are used interchangeably herein. Pre-processor 33 pre-processes the sampled and digitized data to generate pre-processed data.

An image processor 34 receives the pre-processed data from pre-processor 33 and performs image analysis, including that of densitometry and/or absorptiometry through one or more image processing operations. The acquired bone and tissue information, for example, image and density information may be processed and displayed in real time though operations to the image processor 34 and/or the processing unit 36. The processing unit 36 exemplarily operates to store the reconstructed image in a mass storage device 38, where the mass storage device 38 may include, as non-limiting examples, a hard disk drive, a floppy disk drive, a compact disk-read/write (CD-R/W) drive, a Digital Versatile Disc (DVD) drive, a flash drive, and/or a solid-state storage device. As used herein, the term computer is not limited to just those integrated circuits referred to in the art as a computer, but broadly refers to a processor, a microcontroller, a microcomputer, a programmable logic controller, an application specific integrated circuit, and any other programmable circuit, and these terms are used interchangeably herein. It will be recognized that any one or more of the processors and/or controllers as described herein may be performed by, or in conjunction with the processing unit 36, for example through the execution of computer readable code stored upon a computer readable medium accessible and executable by the processing unit 36. For example, the computer/processing unit 36 may include a processor configured to execute machine readable instructions stored in the mass storage device 38, which can be non-transitory memory. Processor unit/computer 36 may be single core or multi-core, and the programs executed thereon may be configured for parallel or distributed processing. In some embodiments, the processing unit 36 may optionally include individual components that are distributed throughout two or more devices, which may be remotely located and/or configured for coordinated processing. In some embodiments, one or more aspects of the processing unit 36 may be virtualized and executed by remotely-accessible networked computing devices configured in a cloud computing configuration. According to other embodiments, the processing unit/computer 36 may include other electronic components capable of carrying out processing functions, such as a digital signal processor, a field-programmable gate array (FPGA), or a graphic board. According to other embodiments, the processing unit/computer 36 may include multiple electronic components capable of carrying out processing functions. For example, the processing unit/computer 36 may include two or more electronic components selected from a list of electronic components including: a central processor, a digital signal processor, a field-programmable gate array, and a graphic board. In still further embodiments the processing unit/computer 36 may be configured as a graphical processing unit (GPU) including parallel computing architecture and parallel processing capabilities.

Processing unit 36 also receives commands and scanning parameters from a user, such as an operator, via a console 40 that includes a user interface device, such as a keyboard, mouse, voice-activated controller, touchscreen or any other suitable input apparatus. An associated display 42 allows a user, such as an operator, to observe the image and densitometry data from processing unit 36. The commands and scanning parameters are used by processing unit 36 to provide control signals and information the imaging controller 26, including the DAS 32, x-ray controller 28, and gantry motor controller 30. In addition, processing unit 36 may operate a table motor controller 44 exemplarily of the imaging controller 26 which controls a movable subject support, which is exemplarily a motorized table 46, to position subject 22 within gantry 12. Particularly, table motor controller 44 adjusts table 46 to move portions of subject 22.

During operation, the system 10 is configured to operate in either a dual energy x-ray mode or a single energy x-ray mode. In the single energy mode, the x-ray source 14 emits x-rays at a narrow band of energies of a few keV and in the diagnostic imaging range of approximately 20-150 keV. In the dual-energy mode, the x-ray source 14 emits radiation at two or more bands of energy emitted simultaneously or in rapid succession. The x-ray source 14 may also be configured to emit a single broadband energy of more than a few keV over the diagnostic imaging range. The system 10 may be switched between the dual energy mode and the single energy mode by increasing or decreasing the x-ray source 14 voltage and/or current. The system 10 may also be switched between the dual energy mode and the single energy mode with a K-edge filter and energy discriminating detector. It should be noted that the x-ray source 14 may emit x-rays at different energies or ranges of energies.

The x-ray source 14 may be configured to output a fan beam 16 of x-rays. The x-ray source 14 may also be configured to output a pencil beam of x-rays (not shown), a cone beam of x-rays, or other configurations. In some embodiments, the processing unit 36 controls the system 10 to operate in the single energy mode or dual-energy mode to determine the bone or tissue information of at least some of the scanned body. In general, an image resolution in the system 10 may be based on a detector element size, a source focal spot size, and an object to detector distance. The acquired images may then be used to measure, for example, bone density or other bone and tissue characteristics or content. As discussed above, the dual-energy x-ray scan may be a rectilinear scan of the entire patient body, which may be performed in a transverse-type scanning sequence as described above. During the dual-energy x-ray scan an image of the entire body of the patient may be acquired, which includes image information relating to the bones and tissue in the body. The full body or total body scan of the entire body may be performed as a single scanning operation, which may be a low dose mode scan. In some embodiments, instead of a full body or total body scan, individual rectangular regions of the body may be scanned, which may be single sweep scans. Once the scan of the patient, or a portion thereof, is completed, the dual energy signals provided by the detector 18 are deconstructed into images of two basis materials, such as bone and soft tissue. The high and low energy signals can also be combined to provide a single energy mode having superior signal to noise ratio for imaging purposes.

The system 10 additionally includes a camera 80 disposed on a surface 82 of the room within which the system 10 is located. In the exemplary embodiment of FIGS. 3-5, the camera 80 is disposed in a ceiling 84 above the system 10, such that the system 10 and imaged volume 31 are entirely positioned within the area viewable by the camera 80, which defines the camera referential 83. The camera 80 is operably connected to the computer/processing unit 36 to forms a part of a camera-based feature detection system 85 for the system 10 that can be operated to detect and provide information regarding the proper positioning of the patient 22 on the table 20, automatic positioning of the source 14 and detector 18 relative to the area of interest of the patient 22, and/or the determination of the current field of view (FOV) of the source 14 relative to the position of the patient 12. The camera 80 can be operated in response to signals sent from the computer/processing unit 36 to the camera 80, with the data forming the images obtained by the camera 80 being able to be transmitted to the computer/processing unit 36. The camera 80 can be any suitable type of camera for obtaining images of the system 10 and the patient 22 located on the system 10, such as an RBG-IR-Depth camera capable of obtaining images in the visible and infrared spectrums, and providing depth information among others.

The images from the camera 80 are transmitted to the camera-based feature detection system 81 within the computer/processing unit 36 which can be utilized to provide information of one or more of the proper positioning of the patient 22 on the table 20, automatic positioning of the source 14 and detector 18 relative to the patient 22, and/or the determination of the current field of view (FOV) of the source 14 relative to the position of the patient 22. This information is calculated utilizing a known relationship or registration between the frame of reference for the system 10 or system referential 33, as defined by the components of the system 10, e.g., the gantry 12, the source 14 and the detector 18, and the frame of reference for the camera 80 or camera referential 83, as defined by the location of the camera 80. With this known relationship, the computer/processing unit 36 can correlate information/data provided by the images from the camera 80, e.g., the location of the patient 22 and/or body part of interest (e.g., a knee) on the table 20, with the known location of the source 14 and detector 18 from the system 10 in order to make adjustments to the position of the source 14/detector 18 and/or patient 22/table 20 prior to and/or during any imaging procedure performed on the patient 22 using the system 10.

Figure 5:
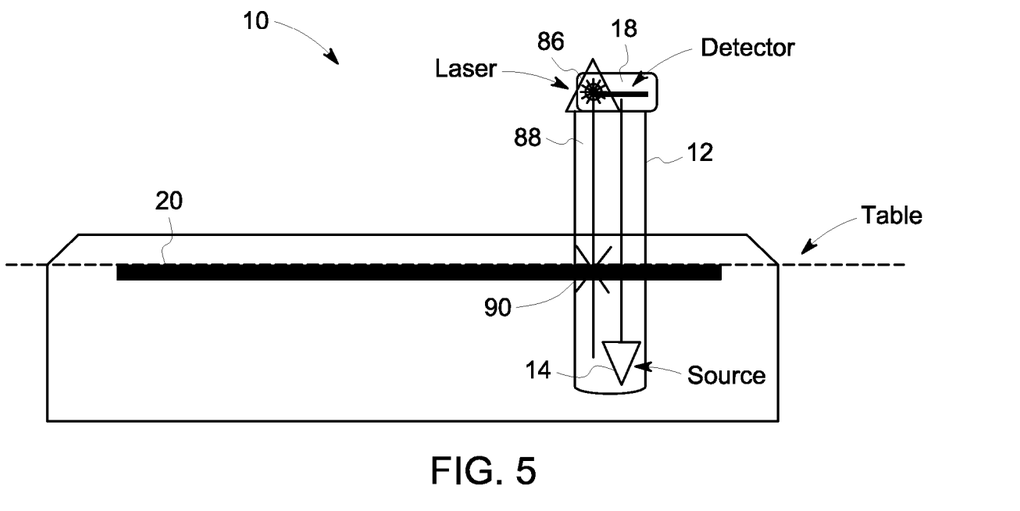
FIG. 5 is a schematic view of the positioning laser utilized with the DXA system of FIG. 4 according to an exemplary embodiment of the disclosure.

In order to provide the known relationship between the system referential and the camera referential, there must be a registration or calibration of the position of the system 10 and the components thereof within the camera referential 83. As best shown in FIG. 5, the upper end 15 of the gantry 12 includes a light source 85, such as a target laser 86 disposed adjacent the detector 18. When operated, the laser 86 projects a light beam 88 onto the table 20 or portion of the patient 22 on the table 20 to provide an indication 90 of the point where the x-rays from the source 14 are to pass through the table 20 on a path to the detector 18.

Figure 6:
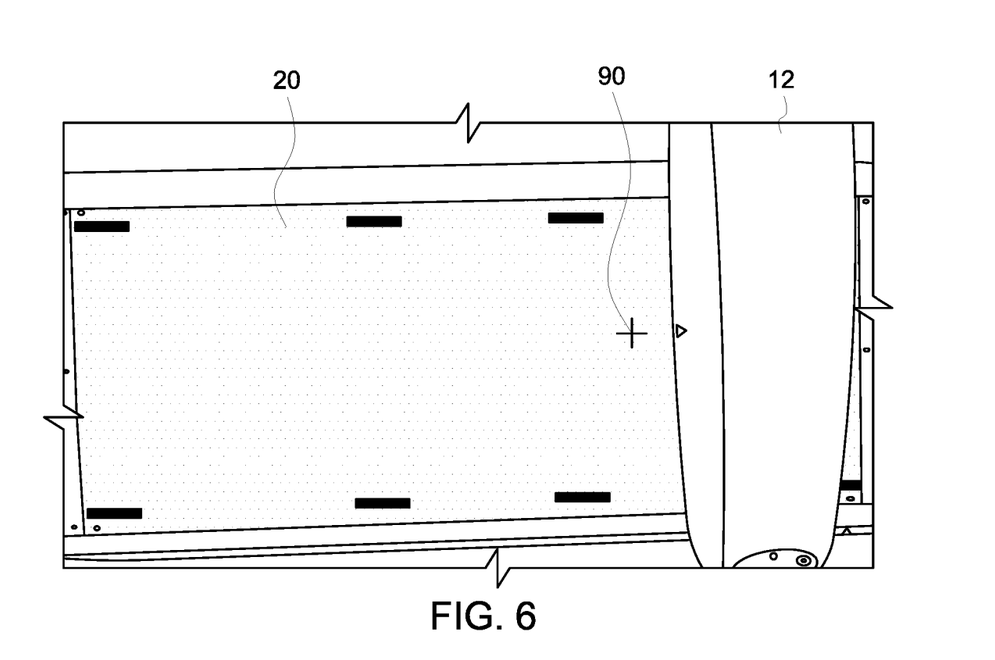
FIG. 6 is a top plan view of the positioning laser as viewed from the external camera in a calibration procedure for the camera feature detection system and calibration system of FIG. 4 according to an exemplary embodiment of the disclosure.
Figure 7:
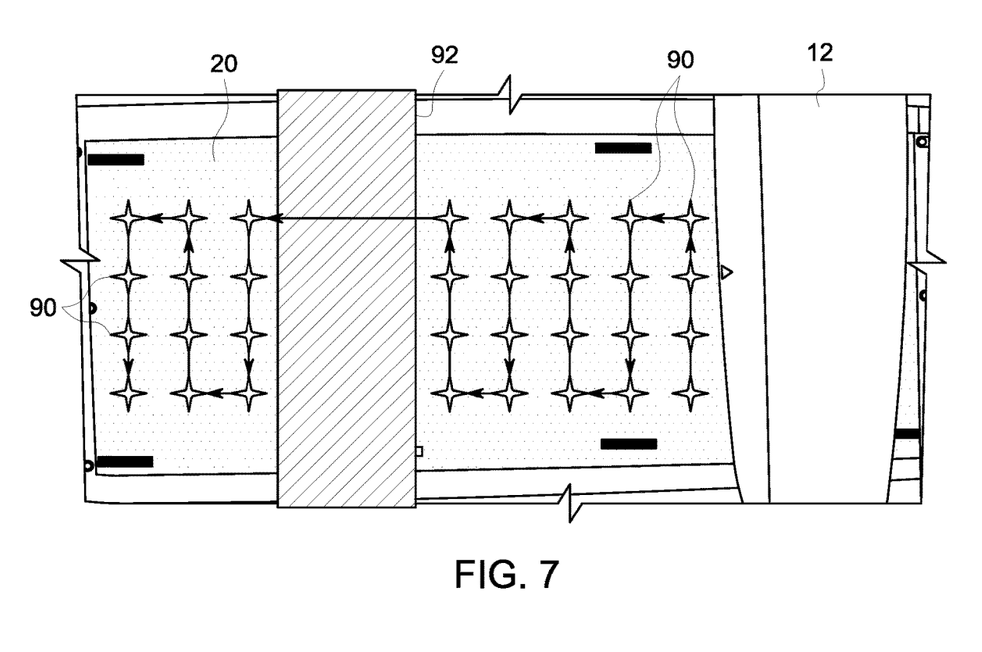
FIG. 7 is a schematic view of the movement of the positioning laser and detector of the DXA system of FIG. 4 as viewed from the external camera in performing the calibration procedure for the camera feature detection system and calibration system according to an exemplary embodiment of the disclosure.

When the laser 86 is operated, as best shown in FIG. 6 the location of the indication 90 generated by the laser 86 relative to the components of the system 10, e.g., the source 14, detector 18 and table 20, is known within the system referential 33 as a result of the construction of the system 10 and the positioning of the components under the control of the computer/processing unit 36. Further, the position of the indication 90 can also be determined within the camera image referential 83 using an image obtained by the camera 80 of the indication 90 as projected onto the table 20. By moving the gantry 12 along the long axis table 20 and moving the detector 18 within the gantry 12 to move the indication to different points along the short axis of the table 20 as different points along the long axis, as shown in FIG. 7, the camera 80 can obtain a number of images of the indication 90 along the path of the gantry 12, providing multiple reference points for the indication 90 within the camera image referential 83 that have a correspondence with known locations of the indication 90 within the system referential 33. Depending upon the position of the camera 80, there may be an area 92 of the table 20 that is obstructed by the gantry 12 such that the indication 90 cannot be viewed by the camera 80. However, the number of points for the location of the indication 90 that can be obtained to either side of the area 92 are sufficient to calculate the necessary correspondence between the locations of the indication 90 in the system referential 33 and in the camera image referential 83 and thus registering camera referential 83 to system referential 33.

In a particular exemplary embodiment of the invention, each camera image of the indication 90 can be obtained using the camera 80 operated in the visible spectrum and/or in the infrared spectrum, such as when the camera 80 utilized is an Intel® RealSense™ camera, in order to obtain the best view of the location of the indication 90. Using a suitable 2D to 3D pose or model correspondence procedure, the localization in 2D image(s) of the indication 90 obtained by the camera 80, along with the corresponding 3D coordinates of the indication in the system referential can be employed to determine the pose/position of the camera 80 relative to system 10.

Figure 8:
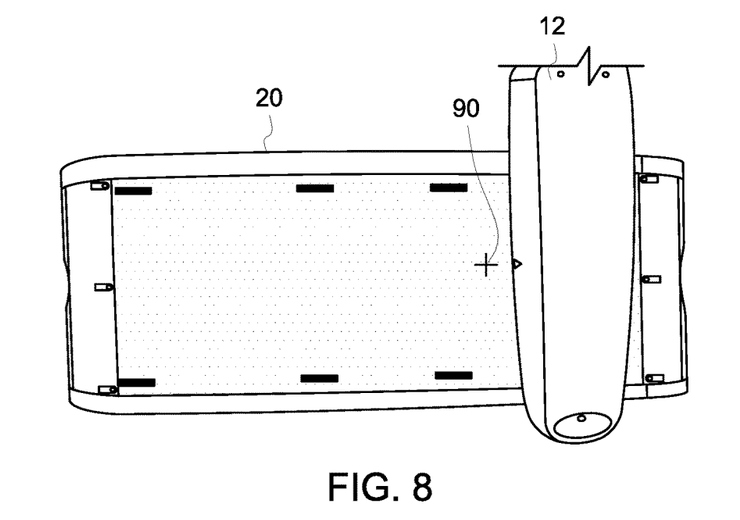
FIG. 8 is a top plan view of the positioning laser as viewed from the external camera in a calibration procedure for the camera feature detection system and calibration system of FIG. 4 according to another exemplary embodiment of the disclosure.

Further, in other exemplary embodiments illustrated in FIG. 8, the location of the indication 90 within the camera image referential 83 can be determined by obtaining a first camera image of the system 10 with no indication 90 present, which can be a first infrared camera image, subsequently operating the laser 86 at the same location for the gantry 12 and obtaining a second camera image of the system 10 including the indication 90, which can be a second infrared image, and then subtracting the pixels in the first image without the indication 90 from the second image including the indication 90 to produce a third image of only the indication 90 within the camera image referential 83.

With the images of the indication 90 from the camera 80 and the corresponding indication coordinates into the system referential 33, with a minimum of three (3) images being required, a transformation matrix can be computed to establish the correspondence of any points in the camera referential 83 to points within the system referential 33. For example, for each camera image, the location of the indication 90 is known in each of the X, Y and Z axes of the system referential 33 as a result of the known location of the laser 86 due to the known position of the gantry 12 based on the construction of the gantry 12 (and position of the laser 86 thereon) in conjunction with any movement of the gantry 12 via suitable motors under the control of the imaging controller 32 and/or computer/processing unit 36, thus determining the position of the indication 90 in the X and Y axes, with the Z axis position being defined as 0, i.e., the surface of the table 20. With these known coordinates of the indication 90 in the system referential 33, along with the corresponding location of the indication in the camera image referential 83, it is possible to register the camera referential 83 with regard to the system referential 33 such as by employing any suitable known manner of determining the solution for the Perspective-n-Point (PnP) for the camera 80.

Figure 9:
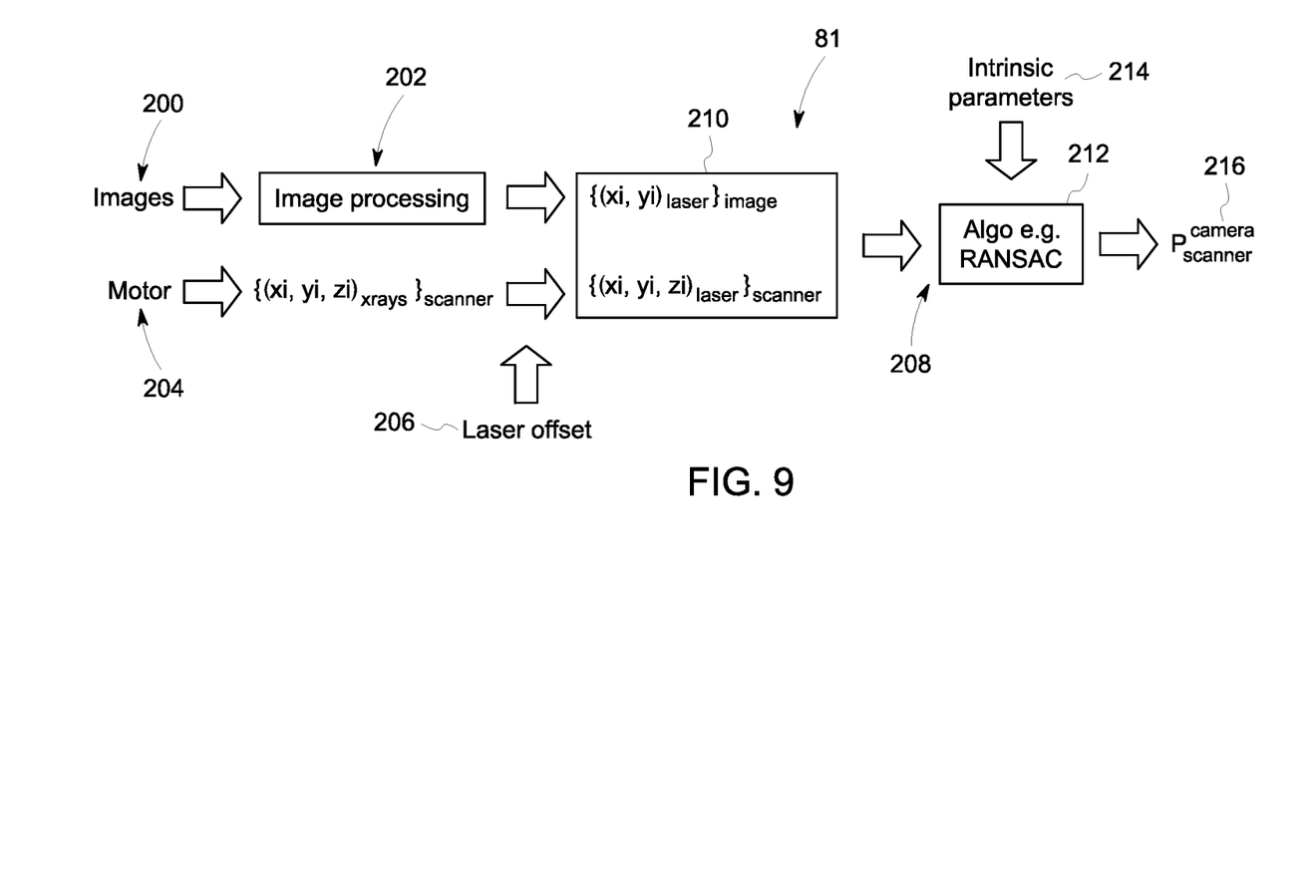
FIG. 9 is a schematic view of a method of operation of the camera feature detection system and calibration system of FIG. 4

For example, as shown in the exemplary embodiment of FIG. 9, the calibration system 81 can be operated in step 200 to obtain one or more camera images of the indication 90, such as described previously and/or in an infrared or visible spectrum modes of operation for the camera 80. In step 202 the one or more images are subjected to image processing by the system 10, such as by the processing unit 36, where the X and Y coordinates of the indication 90 in the image(s) are determined based on image processing algorithms or manual detection. Simultaneously, in step 204 the gantry 12 is moved to a desired location using the one or more motors such that the position of the gantry 12 within the system referential 33 is known based on the precise operation of the motor(s) to position the gantry 12. Correspondingly, the location or coordinates where the emitted x-rays pass through the table 20, i.e., is known from the structure and position of the gantry 12. In step 206, which can be performed prior to, simultaneously with, or subsequent to step 202, the computer/processing unit 36 can utilize the precise location of the laser 86 relative to the detector 18, i.e., the laser offset, to determine the exact position of the indication 90 within the system referential 33 relative to the position of the x-ray intersection point on the table 20. This process through steps 200-204 can be repeated for a number of different locations of the indication 90 on the table 20 to provide a sufficient number of coordinate pairs 210 for the indication 90 in both the camera image referential 83 and the system referential 33, e.g., at least three coordinate pairs for use with a P3P algorithm employed within the calibration system 81.

With a specified number of coordinate pairs, in step 208 the computer/processing unit 36 can provide the coordinate pairs 210 as an input to a suitable algorithm 212, such as a random sample consensus, or RANSAC algorithm, or a PnP solution, or a combination thereof, such as a that described at: https://en.wikipedia.org/wiki/Perspective-n-Point, which is hereby expressly incorporated herein by reference in its entirety for all purposes, along with various intrinsic parameters 214 for the camera 80, in order to create or output from the artificial intelligence/algorithm 208 a transformation matrix 216 for converting coordinates in the system referential 33 to the camera referential 83 and vice versa.

Figure 10:
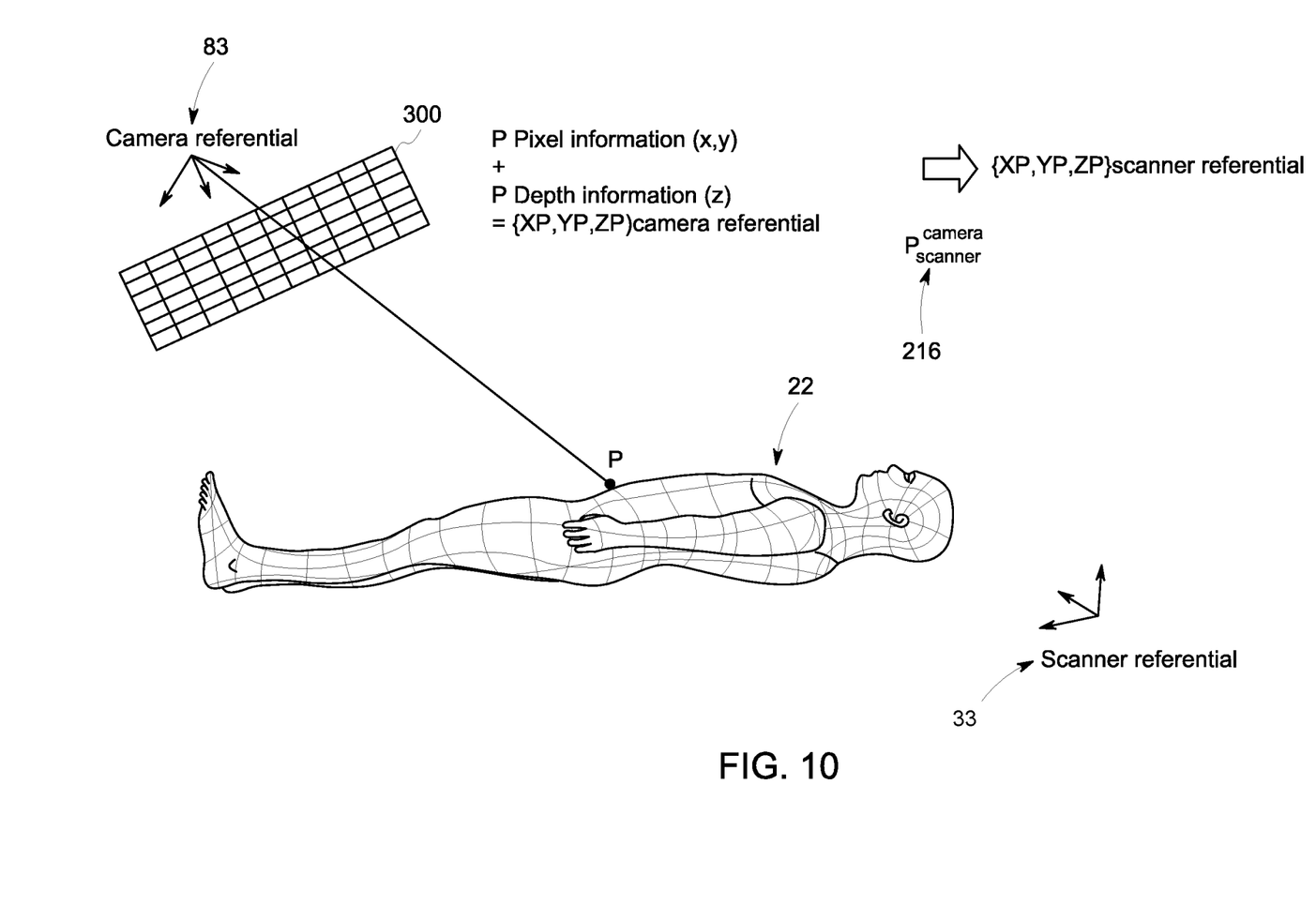
FIG. 10 is a schematic view of the method of operation of the calibration system to register coordinates of a point in a camera referential with coordinates for the point within a system referential.

Looking now at FIG. 10, this transformation matrix 216/registration enables the computer/processing unit 36 to associate images from the camera 80 with images and/or proposed images from the detector 18 in order to accurately identify the position of anatomical structures of the patient 22 shown in a camera image within the system referential 33. In particular, in a camera image 300 obtained by the camera 80 of a point of interest P on the patient/subject 22, the image provides pixel information (X,Y) and depth information (Z) on the point of interest P that provides coordinates (X,Y,Z) for the point of interest P in the camera referential 83. The transformation matrix 216 can be applied to the coordinates for the point P in the camera referential 83 to convert the coordinates into coordinates within the system referential 33 for use by the system 10.

Further, as the system and method requires no additional components for the performance of the camera calibration, i.e., no optical marker, the camera calibration system and method of the present disclosure provides a much more highly efficient calibration process than employed previously.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for calibrating a camera-based feature detection system for an x-ray system, the method comprising the steps of:
   a. providing an x-ray system comprising:
      i. a support surface, and a gantry operably connected to the support surface and including an x-ray source, an x-ray detector alignable with the x-ray source, and a light source disposed on the gantry adjacent the x-ray detector, the gantry defining a system referential;
      ii. an image processing system operably connected to the gantry to control operation of the light source, and the x-ray source and x-ray detector to generate x-ray image data, the image processing system including a processing unit for processing the x-ray image data from the detector, a database operably connected to the processing unit and storing instructions for operation of a calibration system, a display operably connected to the image processing system for presenting information to a user, and a user interface operably connected to the image processing system to enable user input to the image processing system; and
      iii. a camera-based feature detection system including a camera spaced from the gantry and operably connected to the image processing system, the camera defining a camera referential within which the support surface and gantry are positioned and operable to generate one or more camera images of the support surface and gantry, wherein the calibration system is operable to register the camera referential to the system referential;
   b. operating the light source to position an indication on the support surface;
   c. obtaining a number of camera images of the indication on the support surface;
   d. determining a number of positions of the indication within the camera image referential;
   e. determining a number of positions of the indication within the system referential; and
   f. registering the camera referential to the system referential.

2. The method of claim 1, wherein the step of registering the camera referential to the system referential comprises determining a transformation matrix between the camera referential and the system referential.

3. The method of claim 2, wherein the step of determining a transformation matrix between the camera referential and the system referential comprises the steps of:

a. providing the number of positions of the indication within the camera image referential to an algorithm within the calibration system;
g. providing the number of positions of the indication within the system referential to the algorithm within the calibration system; and
b. operating the calibration system to produce the transformation matrix.

4. The method of claim 3, wherein the algorithm is a perspective-n-point solution algorithm.

5. A method for calibrating a camera-based feature detection system for an x-ray system, the method comprising the steps of:
   a. providing an x-ray system comprising:
      i. a support surface, and a gantry operably connected to the support surface and including an x-ray source, an x-ray detector alignable with the x-ray source, and a light source disposed on the gantry adjacent the x-ray detector, the gantry defining a system referential;
      ii. an image processing system operably connected to the gantry to control the operation of laser, and the x-ray source and x-ray detector to generate x-ray image data, the image processing system including a processing unit for processing the x-ray image data from the detector, a database operably connected to the processing unit and storing instructions for operation of a calibration system, a display operably connected to the image processing system for presenting information to a user, and a user interface operably connected to the image processing system to enable user input to the image processing system; and
      iii. a camera-based feature detection system including a camera spaced from the gantry and operably connected to the image processing system, the camera defining a camera referential within which the support surface and gantry are positioned and operable to generate one or more camera images of the support surface and gantry, wherein the calibration system is operable to register the camera referential to the system referential;
   b. operating the light source to position an indication on the support surface;
   c. obtaining a number of camera images of the indication on the support surface;
   d. determining a number of positions of the indication within the camera image referential;
   e. determining a number of positions of the indication within the system referential; and
   f. registering the camera referential to the system referential, wherein the light source is a laser and wherein the step of determining the position of the indication within the system referential comprises:
      a. determining a position of the detector within the system referential;
      b. determining a position of the laser within the system referential relative to the position of the detector; and
      c. determining the position of the indicator within the system referential relative to the position of the laser.

6. The method of claim 1, wherein the step of determining the position of the indication within the system referential relative to the detector comprises applying a light source offset to the position of the detector.

7. The method of claim 6 wherein the light source offset is a difference between a position of the detector on the gantry and a position of the light source on the gantry.

8. The method of claim 1, wherein the step of obtaining the camera image of the indication comprises the step of obtaining either an RGB or an infrared camera image of the indication on the support surface.

9. The method of claim 1, further comprising the steps of:
   a. operating the light source to position the indication on a first location on the support surface;
   b. obtaining first camera image of the indication at the first location on the support surface
   c. moving the gantry relative to the support surface after obtaining the first camera image;
   d. operating the light source to position the indication at a second location on the support surface;
   e. obtaining a second camera image of the indication at the second location on the support surface.

10. The method of claim 9, wherein the step of moving the gantry relative to the support surface comprises moving the gantry along at least one of a long axis of the support surface or a short axis of the support surface.

11. The method of claim 9, wherein the step of moving the gantry relative to the support surface comprises moving the gantry in a raster pattern over the support surface.

12. The method of claim 9, further comprising the step of repeatedly moving the gantry to obtain camera images of the indication at a minimum number of locations on the support surface.

13. The method of claim 12, further comprising the step of repeatedly moving the gantry to obtain camera images of the indication in at least three locations on the support surface.

14. The method of claim 1, wherein no optical marker is attached to the support surface or gantry.

15. The method of claim 1, wherein the x-ray system is a DXA system.

16. An x-ray system comprising:
   i. a support surface, and a gantry operably connected to the support surface and including an x-ray source, an x-ray detector alignable with the x-ray source, and a light source disposed on the gantry adjacent the x-ray detector, the gantry defining a system referential;
   ii. an image processing system operably connected to the gantry to control the operation of the light source, and the x-ray source and x-ray detector to generate x-ray image data, the image processing system including a processing unit for processing the x-ray image data from the detector, a database operably connected to the processing unit and storing instructions for operation of a calibration system, a display operably connected to the image processing system for presenting information to a user, and a user interface operably connected to the image processing system to enable user input to the image processing system; and
   iii. a camera-based feature detection system including a camera spaced from the gantry and operably connected to the image processing system, the camera defining a camera referential within which the support surface and gantry are positioned and operable to generate one or more camera images of the support surface and gantry, wherein the calibration system is operable to register the camera referential to the system referential;
   wherein the calibration system is configured to determine a number of positions of the indication within the camera image referential, to determine a number of positions of the indication within the system referential, and to register the camera referential to the system referential.

17. The x-ray system of claim 16, wherein the x-ray system does not include an optical marker.

18. The x-ray system of claim 17, wherein the calibration system is configured to register the camera referential to the system referential by determining a transformation matrix between the camera referential and the system referential.

19. The x-ray system of claim 16, wherein the camera is capable of obtaining camera images in visible and infrared spectrums.

20. The method of claim 16, wherein the calibration system is configured to register the camera referential to the system referential by determining a transformation matrix between the camera referential and the system referential.

* * * * *